(12) United States Patent
Furrer et al.

(10) Patent No.: US 7,935,848 B2
(45) Date of Patent: May 3, 2011

(54) BUTONE DERIVATIVES USEFUL AS COOLING AGENTS

(75) Inventors: Stefan Michael Furrer, Cincinnati, OH (US); David Max Dastrup, Liberty Township, OH (US); Thomas Scott McCluskey, Amelia, OH (US)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 12/599,122

(22) PCT Filed: May 14, 2008

(86) PCT No.: PCT/CH2008/000219
§ 371 (c)(1),
(2), (4) Date: Dec. 7, 2009

(87) PCT Pub. No.: WO2008/141469
PCT Pub. Date: Nov. 27, 2008

(65) Prior Publication Data
US 2010/0197713 A1    Aug. 5, 2010

Related U.S. Application Data

(60) Provisional application No. 60/931,338, filed on May 23, 2007.

(51) Int. Cl.
*C07C 49/213* (2006.01)
*C07D 213/46* (2006.01)
*A61K 31/12* (2006.01)
*A61K 31/435* (2006.01)
(52) U.S. Cl. .......................... 568/308; 546/340; 514/679
(58) Field of Classification Search .................. 568/308; 546/340; 514/679
See application file for complete search history.

(56) References Cited

U.S. PATENT DOCUMENTS

| | | | |
|---|---|---|---|
| 3,870,759 | A | 3/1975 | Inamoto et al. |
| 4,136,163 | A | 1/1979 | Watson et al. |
| 4,150,052 | A | 4/1979 | Watson et al. |
| 7,632,964 | B2 | 12/2009 | Furrer et al. |
| 2008/0311232 | A1 | 12/2008 | Furrer et al. |

FOREIGN PATENT DOCUMENTS

| | | |
|---|---|---|
| EP | 0885 869 A | 12/1998 |
| GB | 1 457 671 A | 12/1976 |
| GB | 1457671 A | 12/1976 |
| WO | WO 2005/049553 A1 | 6/2005 |
| WO | WO 2006/125334 A1 | 11/2006 |
| WO | WO 2007/019719 A | 2/2007 |

OTHER PUBLICATIONS

Cai, Yudong. et al., "Carbon-carbon bond formation by radical addition-fragmentation reactions of *O*-alkylated enols", Organic Biomolecular Chemistry, 2004, vol. 2, pp. 2517-2529, XP-0020500533.
Dubois, J. E., et al., "Condensation Chlorure D'Acide-Organomagnesien en Presence D'Halogenure Cuivreaux: Competition des Reactions Heterolytique et Homolytique, Synthese de Cetones Aliphatiques Reamifiees", Tetrahdron, vol. 29, 1973, pp. 3943-3957, XP-0020500535.
Matsumoto, Makoto., et al., "Structure of Ilicicolin H, An Antifungal Antibiotic", Tetrahdron, vol. 42, 1976, pp. 3827-3830, XP-0020500536.
Nakamura, Eiichi, et al., "A Novel Ring-Opening Reaction, An Improved Method for Reductive Succinoylation", Journal of Organic Chemistry, Nov. 25, 1977, vol. 42, No. 25, pp. 4166-4167.
Raw, Andre, et al., "Synthesis of *cis*-1,2-Cyclobutanediols via Intramolecular Pinacol Coupling of 4-Oxo Aldehydes", Journal of Organic Chemistry, 1991, vol. 56, No. 2, pp. 830-833.
Shimada, Junichi, et al., "Ring Expansion and Cleavage of Succinoin Derivatives. Geminal Acylation, Reductive Succinoylation, and Stereoselective Spiro Annelation Methods", Journal of the American Chemical Society, 1984, vol. 106, No. 6, pp. 1759-1773.
Watson, H.R., et al., "New Compounds With the Menthol Cooling Effect", Journal of the Socity Cosmetic Chemisis, Jan. 1, 1978, vol. 29, No. 4, pp. 185-200, XP-009045124.
PCT/CH2008/000219—Written Opinion of the International Searching Authority, Dec. 19, 2008.
PCT/CH2008/000219—International Search Report, Dec. 19, 2008.
GB 0713581.7—Great Britain Search Report, Oct. 26, 2007.
H.R. Watson, et al., New Compounds With the Menthol Cooling Effect, J. Soc. Cosmet. Chem. 29 185 200(1978), p. 185-200.

*Primary Examiner* — Sikarl A Witherspoon
(74) *Attorney, Agent, or Firm* — Curatolo Sidoti Co., LPA; Joseph G. Curatolo; Salvatore A. Sidoti

(57) ABSTRACT

Cooling compounds of formula (I)

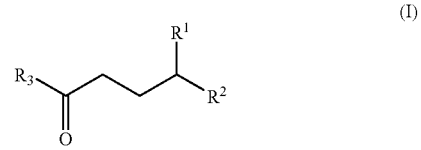

wherein $R^1$ is selected from the group consisting of hydrogen, methyl, $C_1$-$C_3$ alkoxy, phenyl, $C_1$-$C_3$ alkylphenyl, $C_1$-$C_3$ alkoxyphenyl, thienyl, pyridyl, furyl, and indoyl;
$R^2$ is selected from the group consisting of hydrogen and hydroxyl, or
$R^2$ forms together with the carbon atom to which it is attached a carbonyl group; and
$R^3$ is selected from the group consisting of 2,4-dimethylpent-3-yl, 2,3,4-trimethylpent-3-yl, adamantyl and 2-isopropyl-5-methyl-cyclohexyl-1-yl; and, product compositions comprising them.

5 Claims, No Drawings

BUTONE DERIVATIVES USEFUL AS COOLING AGENTS

CROSS REFERENCE TO RELATED APPLICATIONS

This application is a national stage application of International Application No. PCT/CH2008/000219, filed 14 May 2008, which claims the benefit of U.S. Patent Application Ser. No. 60/931,338, filed 23 May 2007, from which applications priority is claimed, and which are incorporated herein by reference.

Disclosed are cooling compounds, that is, compounds that impart a cooling sensation to the skin or the mucous membranes of the body.

In the flavor and fragrance industry there is an ongoing demand for compounds having unique cooling properties that provide the user with a pleasing cooling effect and which are suitable for use in a variety of products, particularly in ingestible and topical products.

Cooling compounds are well known to the art and are widely used in a variety of products such as foodstuffs, tobacco products, beverages, chewing gum, dentifrices, mouthwashes and toiletries.

There has been discovered a new class of cooling compounds. Accordingly, there is disclosed herein a method of providing a cooling sensation to the skin or mucous membranes of the mouth by applying thereto a quantity of at least one chemical compound sufficient to cause a desirable degree of cooling sensation, the chemical compound comprising a compound of formula (I):

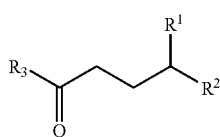

wherein $R^1$ is selected from the group consisting of hydrogen, methyl, $C_1$-$C_3$ alkoxy, phenyl, $C_1$-$C_3$ alkylphenyl (e.g. methylphenyl, ethylphenyl, isopropylphenyl), $C_1$-$C_3$ alkoxyphenyl (e.g. ethoxyphenyl), thienyl, pyridyl (pyrid-2-yl, pyrid-3-yl, pyrid-4-yl), furyl, and indoyl;
$R^2$ is selected from the group consisting of hydrogen and hydroxyl, or $R^2$ forms together with the carbon atom to which it is attached a carbonyl group; and
$R^3$ is selected from the group consisting of 2,4-dimethylpent-3-yl, 2,3,4-trimethylpent-3-yl, adamantyl and 2-isopropyl-5-methyl-cyclohexyl-1-yl (preferably (1R, 2S, 5R).

The compounds of formula (I) may comprise one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC or by stereoselective syntheses.

Non limiting examples are compounds of formula (I) wherein $R^3$ is 2-isopropyl-5-methyl-cyclohexyl-1-yl.

In particular, embodiments are compounds of formula (I) selected from 1-((1R,2S,5R)-2-isopropyl-5-methylcyclohexyl)butan-1-one, 1-((1R,2S,5R)-2-isopropyl-5-methylcyclohexyl)-4-phenylbutan-1-one, 1-((1R,2S,5R)-2-isopropyl-5-methylcyclohexyl)-4-(pyridin-2-yl)butan-1-one, 5-isopropyl-5,6-dimethyl-1-phenylheptan-4-one, 1-((2S,5R)-2-isopropyl-5-methylcyclohexyl)-4-methoxybutan-1-one and 1-((2S,5R)-2-isopropyl-5-methylcyclohexyl)pentan-1-one.

The compounds of formula (I) may be used in products that are applied to mucous membranes such as oral mucosa, or the skin, to give a cooling sensation. By "applying" is meant any form of bringing into contact, for example, oral ingestion, topical application or, in the case of tobacco products, inhalation. In the case of application to the skin, it may be, for example, by including the compound in a cream or salve, or in a sprayable composition. There is therefore also provided a method of providing a cooling sensation to the mucous membrane or skin by applying thereto a product comprising an effective amount of a compound as hereinabove described.

Products that are applied to the oral mucosa may include foodstuffs and beverages taken into the mouth and swallowed, and products taken for reasons other than their nutritional value, e.g. tablets, troches, mouthwash, throat sprays, dentifrices and chewing gums. Products that are applied to the skin may be selected from perfumes, toiletries, cosmetic products such as lotions, oils, ointments and bathing agents, applicable to the skin of the human body, whether for medical or other reasons. Accordingly, in a further aspect there is provided a composition comprising an amount of at least one compound of formula (I) sufficient to stimulate the cold receptors in the areas of the skin or mucous membrane with which the composition comes into contact and thereby promote the desired cooling effect. A cooling effect may be achieved upon application of a product, for example, mouthwash or chewing gums, to the mucous membrane, e.g. oral mucosa, comprising less than 5000 ppm, in certain embodiments between 50 and 3000 ppm, such as about 500 ppm, of a compound of formula (I). If used for beverages the addition of about 15 ppm may be sufficient to achieve a cooling effect. For use in cosmetic product, the product may comprise from about 50 to about 5000 ppm. However, it is understood that the skilled person may employ compounds of formula (I) as hereinabove described in amounts outside the aforementioned ranges to achieve sensorial effects.

Particular examples of foodstuffs and beverages may include, but are not limited to, beverages, alcoholic or non-alcoholic, such as fruit juice beverages, fruit liquors, milk drinks, carbonated beverages, refreshing beverages, and health and nutrient drinks; frozen confectionery such as ice creams and sorbets; desserts such as jelly and pudding; confectionery such as cakes, cookies, chocolates, and chewing gum; jams; candies; breads; tea beverages such as green tea, black tea, chamomile tea, mulberry leaf tea, Roobos tea, peppermint tea; soaps; seasonings; instant beverages; snack foods and the like.

Further examples of topical products may include, but are not limited to, skin-care cosmetics, such as cleansing tissues, talcum powders, face creams, lotions, tonics and gels, hand creams, hand- and body lotions, anticellulite/slimming creams and—lotions, lotions, balms, gels, sprays and creams; sunburn cosmetics including sunscreen lotions, balms, gels, sprays and creams; after sun lotions, sprays and creams; soaps, toothpicks, lip sticks, agents for bathing, deodorants and antiperspirants, face washing creams, massage creams, and the like, Thus there is further provided an end-product selected from the group consisting of products that are applied to the oral mucosa and products that are applied to the skin, such as topical products, oral care products, nasal care products, toilet articles, ingestible products and chewing gum, and the like which comprises a product base and an effective amount of at least one cooling compound of formula (I) as defined herein above.

The compounds as hereinabove described may be used alone or in combination with other cooling compounds known in the art, e.g. menthol, menthone, isopulegol, N-ethyl p-menthanecarboxamide (WS-3), N,2,3-trimethyl-2-isopropylbutanamide (WS-23), menthyl lactate, menthone glycerine acetal (Frescolat® MGA), mono-menthyl succinate (Physcool®), mono-menthyl glutarate, O-menthyl glycerine (CoolAct® 10) and 2-sec-butylcyclohexanone (Freskomenthe®), menthane, camphor, pulegol, cineol, mint oil, peppermint oil, spearmint oil, eucalyptus oil, 3-I-menthoxypropane-1,2-diol, 3-I-menthoxy-2-methylpropane-1,2-diol, p-menthane-3,8-diol, 2-I-menthoxyethane-1-ol, 3-I-menthoxypropane-1-ol, and 4-I-menthoxybutane-1-ol. Further examples of cooling compounds can be found e.g. in WO 2005/049553, WO2006/125334 and WO 2007/019719, which are incorporated herein by reference.

The cooling compounds may be employed into the products simply by directly mixing the compound with the product, or they may, in an earlier step, be entrapped with an entrapment material such as polymers, capsules, microcapsules and nanocapsules, liposomes, film formers, absorbents such as cyclic oligosaccharides, or they may be chemically bonded to a substrate, which are adapted to release the cooling compound upon application of an external stimulus such as temperature, enzyme or the like, and then mixed with the product. Or they may be added while being solubilized, dispersed, or diluted using alcohols or polyhydric alcohols, such as, glycerine, propylene glycole, triazethine and mygliol, natural gums such as gum Arabic, or surfactants, such as glycerine fatty acid esters and saccharide fatty acid esters.

Most of the compounds as hereinabove described are novel in its own right. Thus, there is therefore also provided a compound of the formula (I)

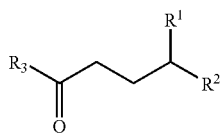
(I)

wherein $R^1$ is selected from the group consisting of hydrogen, methyl, $C_1$-$C_3$ alkoxy, phenyl, $C_1$-$C_3$ alkylphenyl (e.g. methylphenyl, ethylphenyl, isopropylphenyl), $C_1$-$C_3$ alkoxyphenyl (e.g. ethoxyphenyl), thienyl, pyridyl (pyrid-2-yl, pyrid-3-yl, pyrid-4-yl), furyl, and indoyl;
$R^2$ is selected from the group consisting of hydrogen and hydroxyl, or $R^2$ forms together with the carbon atom to which it is attached a carbonyl group; and
$R^3$ is selected from the group consisting of 2,4-dimethylpent-3-yl, 2,3,4-trimethylpent-3-yl, adamantyl and 2-isopropyl-5-methyl-cyclohexyl-1-yl (preferably (1R,2S, 5R);
with the proviso that $R^1$ and $R^2$ are not hydrogen at the same time; and
if $R^1$ is methoxy and $R^2$ forms together with the carbon atom to which it is attached a carbonyl group then $R^3$ is not adamantyl.

The compounds of formula (I) wherein $R^1$ is of such a nature, that it does not interfere with the Grignard reagent, such as alkoxy, phenyl, alkyl phenyl, may be prepared by reaction of the corresponding aldehyde with the appropriate Grignard reagent and subsequent oxidation under conditions known in the art.

Compounds of formula (I) wherein $R^1$ is a heterocyclic ring, such as pyridine, may be prepared using a Sonogashira coupling of halogen-heterocyclic ring, such as 2-bromopyridine, with the appropriate alkyne and subsequent oxidation.

The compositions and methods are now further described with reference to the following non-limiting examples.

These examples are for the purpose of illustration only and it is understood that variations and modifications can be made by one skilled in the art without departing from the spirit and the scope of the invention. It should be understood that the embodiments described are not only in the alternative, but can be combined.

EXAMPLE 1

1-((1R,2S,5R)-2-isopropyl-5-methylcyclohexyl)butan-1-one a) 1-((1R,2S,5R)-2-isopropyl-5-methylcyclohexyl)butan-1-ol To a solution of (1R,2S,5R)-2-isopropyl-5-methylcyclohexanecarbaldehyde (4.64 g, 27.6 mmol) in THF (120 mL) at 0° C. was slowly added propylmagnesium bromide (2 M in THF, 28 mL). After the reaction was allowed to warm to room temperature over 1 h it was again cooled to 0° C. The reaction was quenched with 1 N HCl and partitioned between brine and MTBE. The organic layer was dried (MgSO₄) and concentrated. The residue was purified by silica chromatography to give the desired alcohol (1.65 g).

b) To a solution of 1-((1R,2S,5R)-2-isopropyl-5-methylcyclohexyl)butan-1-ol (0.50 g, 2.4 mmol) in methylene chloride (2.5 mL) were added activated 3 Å molecular sieves (1.5 g) and pyridinium dichromate (1.0 g, 3.5 mmol). The reaction was stirred overnight at room temperature, then filtered through a pad of silica, which was washed with MTBE. After the organic solution was concentrated, the residue was purified by silica chromatography to give the title ketone (379 mg).

$^1$H NMR (300 MHz, CDCl₃) δ 2.48-2.32 (m, 3H), 1.75-1.52 (m, 7H), 1.37-1.33 (m, 1H), 1.04-0.87 (m, 12H), 0.77 (d, 3H); $^{13}$C NMR (75 MHz, CDCl₃) δ 214.8, 54.3, 44.0, 43.9, 38.6, 34.6, 32.4, 28.8, 23.8, 22.3, 21.4, 16.8, 16.0, 13.8.

EXAMPLE 2

1-((1R,2S,5R)-2-isopropyl-5-methylcyclohexyl)-4-phenylbutan-1-one

The title compound was prepared following the general procedure of Example 1 starting from (1R,2S,5R)-2-isopropyl-5-methylcyclohexanecarbaldehyde and (3-phenylpropyl)magnesium bromide.

$^1$H NMR (300 MHz, CDCl₃) δ 7.30-7.15 (m, 5H), 2.64-2.34 (m, 5H), 1.91-1.50 (m, 8H), 1.01-0.72 (m, 12H); $^{13}$C NMR (75 MHz, CDCl₃) δ 214.7, 141.7, 128.5, 128.3, 125.9, 54.4, 44.0, 41.2, 38.8, 35.1, 34.6, 32.5, 28.9, 24.8, 23.8, 22.4, 21.5, 16.0.

EXAMPLE 3

1-((1R,2S,5R)-2-isopropyl-5-methylcyclohexyl)-4-(pyridin-2-yl)butan-1-one a) 1-((1R,2S,5R)-2-isopropyl-5-methylcyclohexyl)but-3-yn-1-ol

To a solution of (1R,2S,5R)-2-isopropyl-5-methylcyclohexanecarbaldehyde (1.0 g, 6.0 mmol) in THF (10 mL) at 0° C. was slowly added propargyl magnesium bromide (1 M, 8.9 mmol). After the reaction was allowed to warm to room temperature overnight 1.5 equivalents of additional propargyl magnesium bromide were added and the reaction was allowed to stir for 6 additional h. The reaction was again cooled to 0° C. and then quenched with 1 N HCl and partitioned between brine and MTBE. The organic layer was dried ($MgSO_4$) and concentrated. The residue was purified by silica chromatography to give the desired alcohol (0.47 g).

b) 1-((1R,2S,5R)-2-isopropyl-5-methylcyclohexyl)-4-(pyridin-2-yl)but-3-yn-1-ol To a round bottom flask were added 1-((1R,2S,5R)-2-isopropyl-5-methylcyclohexyl)but-3-yn-1-ol (0.47 g, 2.3 mmol), triethylamine (10 mL), 2-bromopyridine (0.28 mL, 2.7 mmol), bis(triphenylphosphine)palladium(II) dichloride (16 mg, 0.023 mmol) and copper(I) iodide (9 mg, 0.045 mmol). After this mixture was stirred with heating overnight at 60° C., it was allowed to cool to room temperature. The reaction was mixed directly with silica, concentrated and purified by silica chromatography to give the desired coupling product (286 mg).

c) 1-((1R,2S,5R)-2-isopropyl-5-methylcyclohexyl)-4-(pyridin-2-yl)butan-1-ol A solution of 1-((1R,2S,5R)-2-isopropyl-5-methylcyclohexyl)-4-(pyridin-2-yl)but-3-yn-1-ol (286 mg, 1.00 mmol) in ethanol (6.0 mL) was flushed with nitrogen. Palladium on carbon (10%, 100 mg) was added and the reaction was again flushed with nitrogen. The reaction was then stirred at room temperature under an atmosphere of hydrogen overnight. The reaction was filtered through a pad of silica and purified by silica chromatography to give the desired hydrogenation product (190 mg).

d) 1-((1R,2S,5R)-2-isopropyl-5-methylcyclohexyl)-4-(pyridin-2-yl)butan-1-one To a solution of 1-((1R,2S,5R)-2-isopropyl-5-methylcyclohexyl)-4-(pyridin-2-yl)butan-1-ol (177 mg, 0.61 mmol) in methylene chloride (2.0 mL) were added activated 3 Å molecular sieves (0.75 g) and pyridinium dichromate (0.27 g, 3.5 mmol). The reaction was stirred overnight at room temperature then filtered through a pad of silica, which was washed with MTBE. After the organic solution was concentrated, the residue was purified by silica chromatography to give the title ketone (80 mg).

$^1$H NMR (300 MHz, $CDCl_3$) δ 8.53-8.51 (m, 1H), 7.62-7.56 (m, 1H), 7.17-7.08 (m, 2H), 2.80 (t, 2H), 2.59-2.40 (m, 3H), 2.06-1.98 (m, 2H), 1.71-1.53 (m, 5H), 1.41-1.25 (m, 1H), 1.02-0.93 (m, 3H), 0.89-0.85 (m, 6H), 0.74 (d, 3H); $^{13}$C NMR (75 MHz, $CDCl_3$) δ 214.5, 161.5, 149.2, 136.3, 122.8, 121.0, 54.4, 44.0, 41.2, 38.7, 37.5, 34.6, 32.4, 28.9, 23.8, 23.3, 22.3, 21.4, 16.0.

EXAMPLE 4

5-isopropyl-5,6-dimethyl-1-phenylheptan-4-one

The title compound was prepared following the general procedure of Example 1 starting from 2-isopropyl-2,3-dimethylbutanal and (3-phenylpropyl)magnesium bromide.

$^1$H NMR (300 MHz, $CDCl_3$) δ 7.32-7.19 (m, 5H), 2.64 (t, 2H), 2.41 (t, 2H), 2.04 (sep., 2H), 1.88 (quint, 2H), 1.09 (s, 3H), 1.83 (d, 12H), 1.41-1.25 (m, 1H); $^{13}$C NMR (75 MHz, $CDCl_3$) δ 215.9, 142.0, 128.4, 128.3, 125.8, 56.3, 41.3, 35.3, 32.9, 25.0, 18.2, 17.6.

EXAMPLE 5

1-(2S,5R)-2-isopropyl-5-methylcyclohexyl)-4-methoxybutan-1-one

The title compound was prepared following the general procedure of Example 1 starting from (1R,2S,5R)-2-isopropyl-5-methylcyclohexanecarbaldehyde and (3-methoxypropyl)magnesium bromide.

$^1$H NMR (300 MHz, $CDCl_3$) δ 3.37 (t, 2H), 3.31 (s, 3H), 2.59-2.42 (m, 3H), 1.87-1.54 (m, 8H), 1.04-0.87 (m, 9H), 0.77 (d, 3H);
$^{13}$C NMR (75 MHz, $CDCl_3$) δ 214.5, 71.7, 58.4, 54.6, 43.9, 38.7, 38.3, 34.6, 32.4, 28.9, 23.8, 23.3, 22.3, 21.4, 16.0.

EXAMPLE 6

1-((2S,5R)-2-isopropyl-5-methylcyclohexyl)pentan-1-one

The title compound was prepared following the general procedure of Example 1 starting from (1R,2S,5R)-2-isopropyl-5-methylcyclohexanecarbaldehyde and butyl magnesium bromide.

$^1$H NMR (300 MHz, $CDCl_3$) δ 2.47-2.36 (m, 3H), 1.78-1.49 (m, 7H), 1.34-1.27 (m, 3H), 1.03-0.78 (m, 12H), 0.76 (d, 3H); $^{13}$C NMR (75 MHz, $CDCl_3$) δ 215.1, 54.4, 44.0, 41.8, 38.7, 34.6, 32.5, 28.9, 25.5, 23.8, 22.4, 22.4, 21.4, 16.0, 13.9.

EXAMPLE 7

Cooling Intensity

A small group of panelists was asked to taste various aqueous solutions of compounds of formula (I) and indicate which solutions had a cooling intensity similar to or slightly higher than that of a solution of menthol at 2 ppm. The results are shown in Table 1.

TABLE 1

| Chemical | Concentration | Odor |
|---|---|---|
| Comparison:<br>l-Menthol | 2.0 ppm | Minty |
| Comparison:<br>N-ethyl p-menthanecarboxamide (WS-3) | 1.5 ppm | None |
| 1-((1R,2S,5R)-2-isopropyl-5-methylcyclohexyl)-butan-1-one<br>(Example 1) | 2.0 ppm | None |
| 1-((1R,2S,5R)-2-isopropyl-5-methylcyclohexyl)-4-phenylbutan-1-one<br>(Example 2) | 2.0 ppm | None |
| 1-((1R,2S,5R)-2-isopropyl-5-methylcyclohexyl)-4-(pyridin-2-yl)butan-1-one<br>(Example 3) | 0.01 ppm | None |

TABLE 1-continued

| Chemical | Concentration | Odor |
|---|---|---|
| 5-isopropyl-5,6-dimethyl-1-phenylheptan-4-one (Example 4) | 3.0 ppm | None |

EXAMPLE 8

Application in Toothpaste a) Control, Peppermint Oil

| | |
|---|---|
| Opaque toothgel | 99.20 g |
| Peppermint oil, Terpeneless | 0.50 g |
| Saccharin | 0.30 g |

The chemicals are mixed in the toothgel, a piece of toothgel is put on a toothbrush and a panelist's teeth are brushed. The mouth is rinsed with water and the water is spat out. A cooling sensation is felt by the panelist in all areas of the mouth. The cooling perception lasts for 40 minutes.

b) 1-((1R,2S,5R)-2-isopropyl-5-methylcyclohexyl) butan-1-one (Example 1)

| | |
|---|---|
| Opaque toothgel | 99.15 g |
| Compound of example 1 | 0.05 g |
| Peppermint oil, Terpeneless | 0.50 g |
| Saccharin | 0.30 g |

The chemicals are mixed in the toothgel, a piece of toothgel is put on a toothbrush and a panelist's teeth are brushed. The mouth is rinsed with water and the water is spat out. An intense cooling sensation is felt by the panelist in all areas of the mouth. The cooling perception was rated higher then the control and lasts for 72 minutes.

c) 1-((1R,2S,5R)-2-isopropyl-5-methylcyclohexyl)- 4-phenylbutan-1-one (Example 2)

| | |
|---|---|
| Opaque toothgel | 99.15 g |
| Compound of example 2 | 0.05 g |
| Peppermint oil, Terpeneless | 0.50 g |
| Saccharin | 0.30 g |

The chemicals are mixed in the toothgel, a piece of toothgel is put on a toothbrush and a panelist's teeth are brushed. The mouth is rinsed with water and the water is spat out. An intense cooling sensation is felt by the panelist in all areas of the mouth. The cooling perception was rated higher then the control and lasts for 70 minutes.

EXAMPLE 9

Application in Chewing Gum a) Control, Peppermint Oil

| | |
|---|---|
| Gum Base Solsona-T | 30 g |
| Sorbitol Powder | 50.6 g |
| Maltitol Syrup 85% | 9 g |
| Mannitol Powder | 5 g |
| Glycerin | 5 g |
| Potassium acesulfame (CAS 55589-62-3) | 0.09 g |
| Aspartame | 0.21 g |
| Peppermint oil, terpeneless | 0.50 g |

The gum base and half of the sorbitol were mixed, maltitol syrup was added and the mixed with the gum mass. The rest of powder (rest of sorbitol, mannitol, potassium acesulfame, aspartame) were added and mixed for about 1 minute, when glycerine was added and the gum mass was mix for about 5 minutes, to form the blank chewing gum mass. Peppermint oil was worked into the mass and a piece of the resulting gum (2 g) is chewed by the panelist for 20 min and spat out. A cooling sensation is felt by the panelist in all areas of the mouth. The cooling perception lasts for 50 minutes.

b) 1-((1R,2S,5R)-2-isopropyl-5-methylcyclohexyl) butan-1-one

| | |
|---|---|
| Compound of example 1 | 0.05 g |
| Peppermint oil, terpeneless | 0.50 g |

The chemical and peppermint oil was worked into the blank chewing gum mass from Example 12 a) and a piece of the resulting gum (2 g) is chewed by the panelist for 20 minutes and spat out. A cooling sensation is felt by the panelist in all areas of the mouth. The cooling perception was rated 49% higher then the control and lasts for over 60 minutes.

c) 1-((1R,2S,5R)-2-isopropyl-5-methylcyclohexyl)- 4-phenylbutan-1-one

| | |
|---|---|
| Compound of example 2 | 0.05 g |
| Peppermint oil, terpeneless | 0.50 g |

The chemical and peppermint oil was worked into the blank chewing gum mass from Example 12a) and a piece of the resulting gum (2 g) is chewed by the panelist for 20 minutes and spat out. A cooling sensation is felt by the panelist in all areas of the mouth. The cooling perception was rated 49% higher then the control and lasts for over 60 minutes.

The invention claimed is:
1. A compound selected from the group consisting of 1-((1R,2S,5R)-2-isopropyl-5-methylcyclohexyl)-4-phenylbutan-1-one,

1-((1R,2S,5R)-2-isopropyl-5-methylcyclohexyl)-4-(pyridin-2-yl)butan-1-one,
5-isopropyl-5,6-dimethyl-1-phenylheptan-4-one,
1-((2S,5R)-2-isopropyl-5-methylcyclohexyl)-4-methoxybutan-1-one, and
1-((2S,5R)-2-isopropyl-5-methylcyclohexyl)pentan-1-one.

2. A method of providing a cooling sensation to the skin or mucosa membranes by applying thereto at least one compound selected from the list consisting of
1-((1R,2S,5R)-2-isopropyl-5-methylcyclohexyl)butan-1-one,
1-((1R,2S,5R)-2-isopropyl-5-methylcyclohexyl)-4-phenylbutan-1-one,
1-((1R,2S,5R)-2-isopropyl-5-methylcyclohexyl)-4-(pyridin-2-yl)butan-1-one,
5-isopropyl-5,6-dimethyl-1-phenylheptan-4-one,
1-((2S,5R)-2-isopropyl-5-methylcyclohexyl)-4-methoxybutan-1-one and 1-((2S,5R)-2-isopropyl-5-methylcyclohexyl)pentan-1-one.

3. A product that provides a cooling sensation to the skin or mucous membranes, which product comprises at least one compound selected from the list consisting of
1-((1R,2S,5R)-2-isopropyl-5-methylcyclohexyl)butan-1-one,
1-((1R,2S,5R)-2-isopropyl-5-methylcyclohexyl)-4-phenylbutan-1-one,
1-((1R,2S,5R)-2-isopropyl-5-methylcyclohexyl)-4-(pyridin-2-yl)butan-1-one,
5-isopropyl-5,6-dimethyl-1-phenylheptan-4-one,
1-((2S,5R)-2-isopropyl-5-methylcyclohexyl)-4-methoxybutan-1-one and
1-((2S,5R)-2-isopropyl-5-methylcyclohexyl)pentan-1-one.

4. A method of providing a cooling sensation to the skin or mucosa membranes by applying thereto a product as defined in claim 3.

5. A product selected from the group consisting of products that are applied to the oral mucosa and products that are applied to the skin, comprising a product base and an effective amount of at least one cooling compound selected from the list consisting of
1-((1R,2S,5R)-2-isopropyl-5-methylcyclohexyl)butan-1-one,
1-((1R,2S,5R)-2-isopropyl-5-methylcyclohexyl)-4-phenylbutan-1-one,
1-((1R,2S,5R)-2-isopropyl-5-methylcyclohexyl)-4-(pyridin-2-yl)butan-1-one,
5-isopropyl-5,6-dimethyl-1-phenylheptan-4-one,
1-((2S,5R)-2-isopropyl-5-methylcyclohexyl)-4-methoxybutan-1-one and
1-((2S,5R)-2-isopropyl-5-methylcyclohexyl)pentan-1-one.

* * * * *